(12) United States Patent
Ferris

(10) Patent No.: US 10,368,848 B2
(45) Date of Patent: Aug. 6, 2019

(54) CELL COLLECTION DEVICES

(71) Applicant: Daron G. Ferris, Evans, GA (US)

(72) Inventor: Daron G. Ferris, Evans, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 172 days.

(21) Appl. No.: 15/223,626

(22) Filed: Jul. 29, 2016

(65) Prior Publication Data
US 2017/0049422 A1   Feb. 23, 2017

Related U.S. Application Data

(60) Provisional application No. 62/206,407, filed on Aug. 18, 2015.

(51) Int. Cl.
*A61B 10/02*      (2006.01)
*A61B 10/00*      (2006.01)

(52) U.S. Cl.
CPC .......... *A61B 10/02* (2013.01); *A61B 10/0096* (2013.01); *A61B 2010/0216* (2013.01)

(58) Field of Classification Search
CPC .. A61B 10/02; A61B 10/0096; A61B 10/0216
USPC ........................................................ 600/569
See application file for complete search history.

(56) References Cited

U.S. PATENT DOCUMENTS

| | | | | |
|---|---|---|---|---|
| 4,227,537 A * | 10/1980 | Suciu | ................. | A61B 10/0291 600/569 |
| 4,759,376 A * | 7/1988 | Stormby | .................. | A46B 9/02 15/206 |
| 5,191,899 A * | 3/1993 | Strickland | .......... | A61B 10/0291 600/569 |
| 5,405,755 A * | 4/1995 | Markus | .................. | A61B 10/04 422/294 |
| 5,407,807 A * | 4/1995 | Markus | .................. | A61B 10/04 15/104.2 |
| 5,422,273 A * | 6/1995 | Garrison | ............ | A61B 10/0291 422/547 |
| 7,416,555 B2 * | 8/2008 | Krivoruchko | .... | A61B 17/32072 606/159 |
| 7,954,196 B1 | 6/2011 | Nault-Richter | | |
| 8,011,057 B2 | 9/2011 | Nejat | | |
| 8,108,962 B2 | 2/2012 | Davidson et al. | | |
| 8,323,211 B2 * | 12/2012 | Larkin | ............... | A61B 10/0045 600/562 |
| 2004/0116827 A1 * | 6/2004 | Tiberio | .............. | A61B 10/0045 600/569 |
| 2005/0033194 A1 * | 2/2005 | Fischer | .............. | A61B 10/0045 600/562 |

(Continued)

FOREIGN PATENT DOCUMENTS

CN            101243982 B       8/2010

*Primary Examiner* — Adam J Eiseman
*Assistant Examiner* — H. Q. Nguyen
(74) *Attorney, Agent, or Firm* — Thomas | Horstemeyer, LLP

(57) ABSTRACT

In some embodiments, a cell collection device includes a sample brush including a proximal end, a distal end, and outwardly extending bristles provided at the distal end, and an outer sleeve adapted to receive the sample brush, the sleeve including a proximal end and a distal end, wherein the sleeve can be linearly slid along the length of the brush to encapsulate the bristles after they have been used to collect cells from a patient.

3 Claims, 4 Drawing Sheets

(56) References Cited

U.S. PATENT DOCUMENTS

| | | | |
|---|---|---|---|
| 2009/0240164 A1* | 9/2009 | Gillespie | A61B 10/0291 600/569 |
| 2010/0234763 A1* | 9/2010 | Valdmann | A61B 10/0291 600/569 |
| 2010/0241028 A1 | 9/2010 | Johnson | |
| 2011/0041271 A1 | 2/2011 | Huang | |
| 2011/0087133 A1* | 4/2011 | Ching | A61B 10/0045 600/572 |
| 2013/0158464 A1* | 6/2013 | Samoocha | A61M 27/006 604/8 |
| 2013/0338533 A1* | 12/2013 | Olsen | A61B 10/0291 600/569 |
| 2014/0073988 A1* | 3/2014 | McSherry | A61B 10/0045 600/572 |
| 2014/0330167 A1* | 11/2014 | Speck | A61B 50/30 600/584 |
| 2014/0336528 A1* | 11/2014 | Sethi | A61B 10/0283 600/566 |

* cited by examiner

CELL COLLECTION DEVICES

CROSS-REFERENCE TO RELATED APPLICATION

This application claims priority to U.S. Provisional Application Ser. No. 62/206,407, filed Aug. 18, 2015, which is hereby incorporated by reference herein in its entirety.

BACKGROUND

Anal cancer is a serious disease that affects many. Early detection of anal cancer or pre-cancer is critical. Currently, testing is performed using a cotton or polyethylene terephthalate (PET) swab. The swab is inserted into the anus and the physician moves the swab from side to side while simultaneously rotating the swab about its longitudinal axis. The goal is to collect cells that can be either transferred to a liquid or to a slide to enable examination of the cells under magnification.

There are several disadvantages to the above-described procedure. Although the swabs collect cells well, it can be difficult to transfer those cells to a liquid or a slide because the cells tend to get trapped in the fibers of the swab. Furthermore, the sample technique is relatively complicated and is subject to great variability between physicians. As a consequence of these issues, the swab method has poor sensitivity in detecting cancer. In one study, it was determined that the use of swabs was ineffective in identifying cancer in as many as 92% of anal cancer patients. In addition, swabs can be uncomfortable to patients and, therefore, can provide motivation for such patients to avoid an anal exam.

In view of the above discussion, it can be appreciated that it would be desirable to have an alternative device for collecting cells from the anus for the purpose of screening for anal cancer.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative device for collecting cells from the anus for the purpose of screening for anal cancer. Described herein are cell collection devices that can be used for that purpose and that provide improved results. In some embodiments, a cell collection device includes a sample brush that fits within an outer sleeve. A distal end of the brush extends from a distal end of the sleeve and includes bristles that are optimized for collection of cells from the anorectal transformation zone. The sample brush can be inserted, while within the outer sleeve, into a patient's anus until the bristles are no longer visible and the brush can be rotated about its longitudinal axis to collect cells. Once the sample brush has been withdrawn from the anus, the sleeve can be pushed distally along the length of the brush until the sleeve encapsulates the bristles. The sample brush can then be rotated and/or linearly moved relative to the outer sleeve to separate the cells from the bristles. In some embodiments, this can be performed while the distal end of the sleeve and brush are immersed in a liquid cell collection medium so as to transfer the cells to the medium. Optionally, windows through which the bristles can extend can be provided at the distal end of the sleeve to facilitate such transfer.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
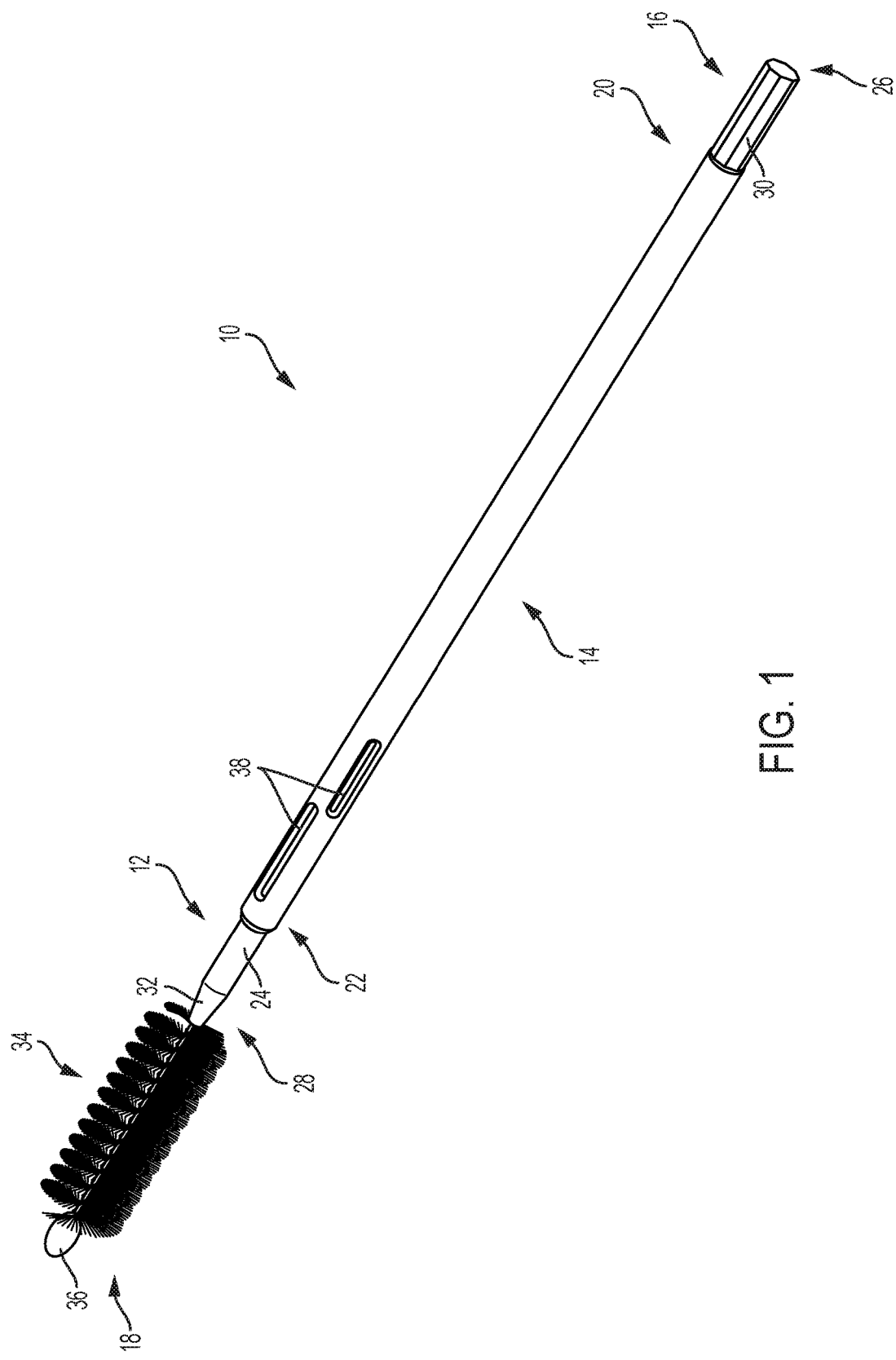
FIG. 1 is a first perspective view of an embodiment of a cell collecting device, showing a sample brush of the device extending from a sleeve of the device to enable cell collection.
Figure 2:
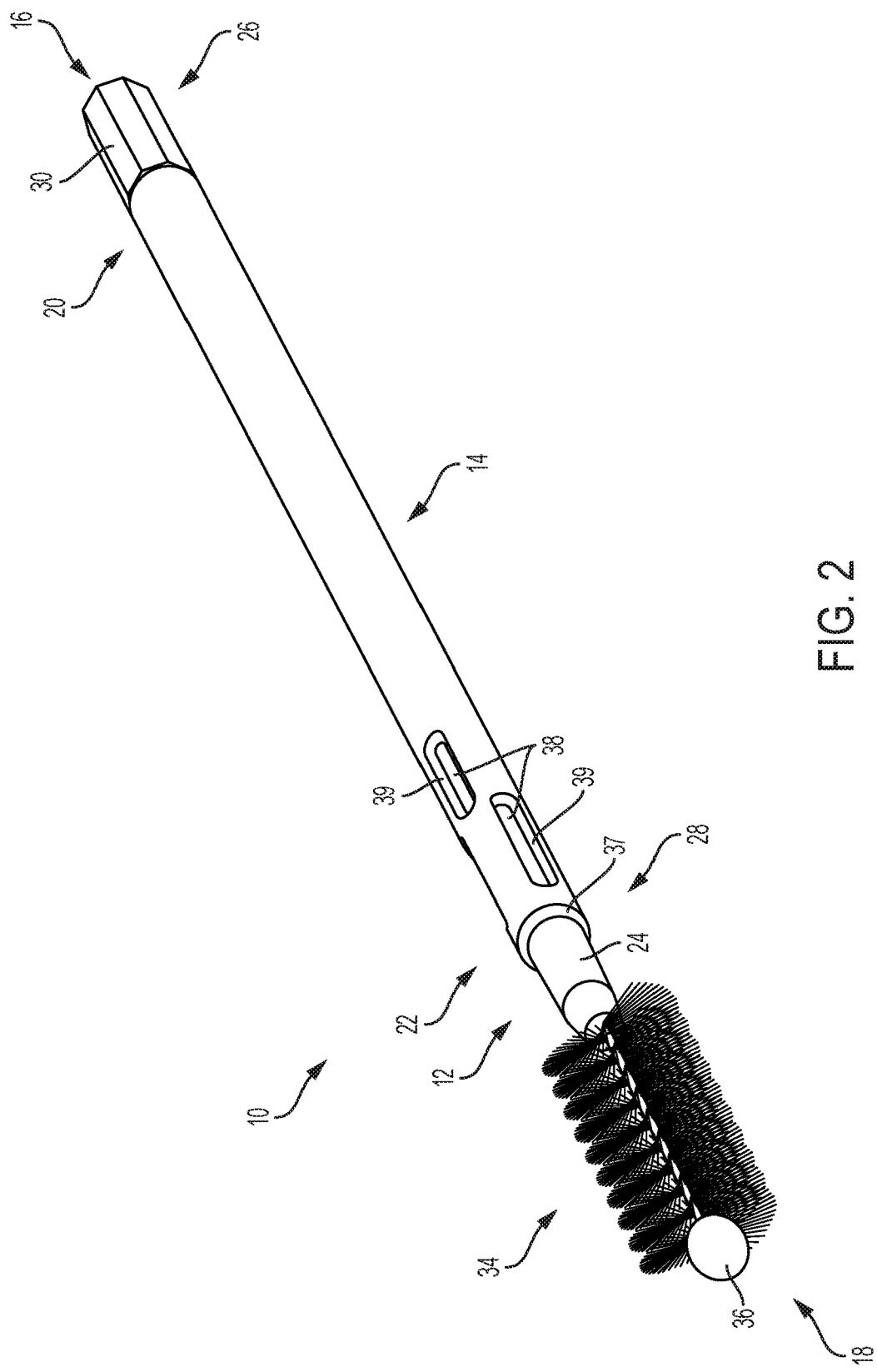
FIG. 2 is a second perspective view of the device of FIG. 1.

FIGS. 1 and 2 illustrate an example cell collection device 10. As shown in these figures, the device 10 generally includes a sample brush 12 that is provided within an outer sleeve 14. The sample brush 12 comprises a proximal end 16 and a distal end 18, and the outer sleeve 14 likewise comprises proximal end 20 and a distal end 22. The sample brush 12 includes an elongated shaft 24 that, in some embodiments, is made of a polymeric material and has a length of approximately 18 to 22 centimeters (cm) and a diameter of approximately 2 to 3 millimeters (mm). The shaft 24 also includes a proximal end 26 and a distal end 28. Positioned at the proximal end 26 of the shaft 24 is a grip element 30 that can be gripped between the fingers of the user (e.g., physician). As shown most clearly in FIG. 1, the distal end 28 of the shaft 24 comprises a tapered portion 32.

Figure 3:
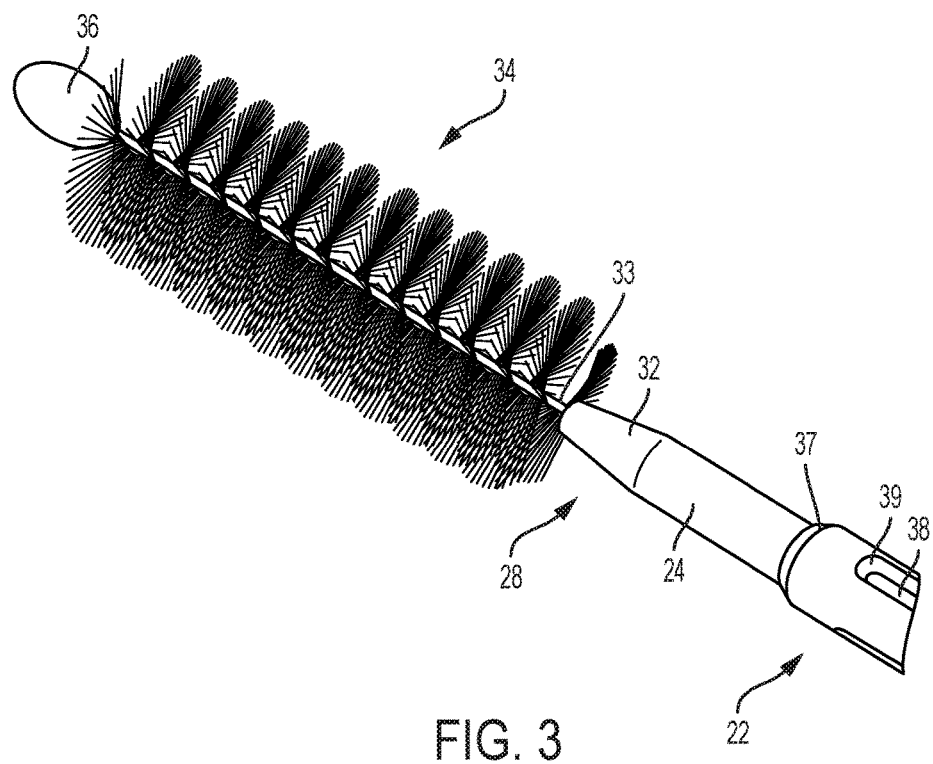
FIG. 3 is detail perspective view of distal ends of the sample brush and sleeve shown in FIG. 1.

Extending axially from the tip of the tapered portion 32 at the distal end 28 of the shaft 24 are twisted wires 33, shown most clearly in FIG. 3, from which cell-collecting bristles 34 extend. The bristles 34 can be made of a polymeric material, such as nylon. In some embodiments, the bristles 34 are arranged in a spiral and extend outward in radial directions from the twisted wires 33 so as to define a circular outer diameter. In some embodiments, this diameter is approximately 1.0 to 1.2 centimeters (cm). In some embodiments, the proximal and distal ends of the bristle section can be tapered to facilitate insertion and removal of the brush 10.

Provided at the distal end of the twisted wires 33 beyond the bristles 34 is a contoured tip 36. In the illustrated embodiment, the tip 36 has an elliptical shape in which the longest dimension of the tip aligns with the longitudinal axis of the shaft 24. In some embodiments, the tip 36 is also made of a polymeric material and has a lateral diameter of approximately 4 to 5 mm. In some embodiments, the length of the "insertion section," which includes the bristles 34 and the tip 36, is approximately 4.0 to 4.5 cm long. As is discussed below, that length is the approximate insertion depth of the sample brush 12.

With further reference to FIGS. 1 and 2, the outer sleeve 14 is formed as a hollow, elongated, cylindrical tube that, for example, can be made of a polymeric material. In some embodiments, the sleeve 14 can have an outer diameter of approximately 5 to 6 mm, an inner diameter of approximately 3.5 to 4 mm, and a length of approximately 10 to 15 cm. As shown most clearly in FIG. 2, the distal tip of the sleeve 14 can include a sharp beveled edge 37 that, as described below, facilitates the transfer of collected cells. As indicated in both FIGS. 1 and 2, the distal end 22 of the sleeve 14 can also include one or more bristle windows 38 through which the bristles 34 of the sample brush 12 can extend when the insertion section is retracted into the sleeve. Like the distal tip of the sleeve 14, these windows 38 can include sharp beveled edges 39 that facilitate the transfer of collected cells.

Figure 4:
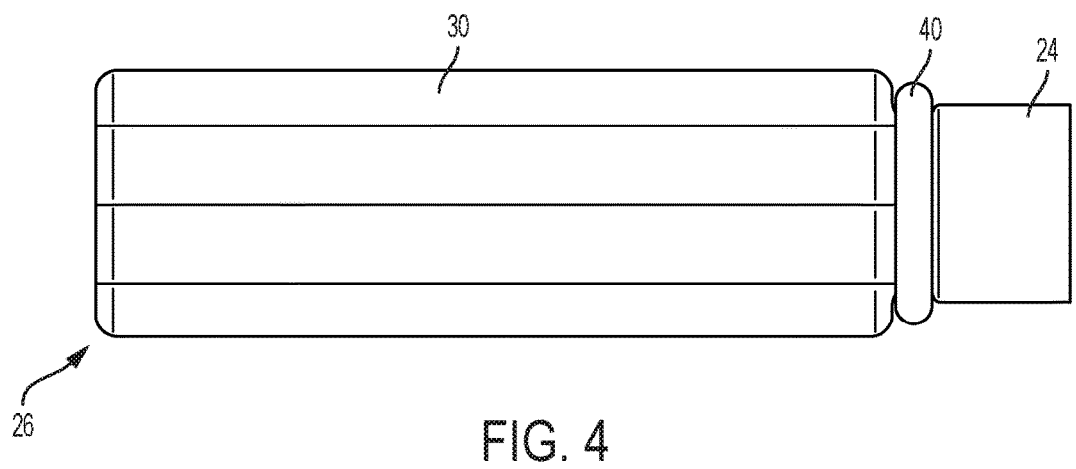
FIG. 4 is a detail side view of a proximal end of the sample brush shown in FIG. 1.
Figure 5:
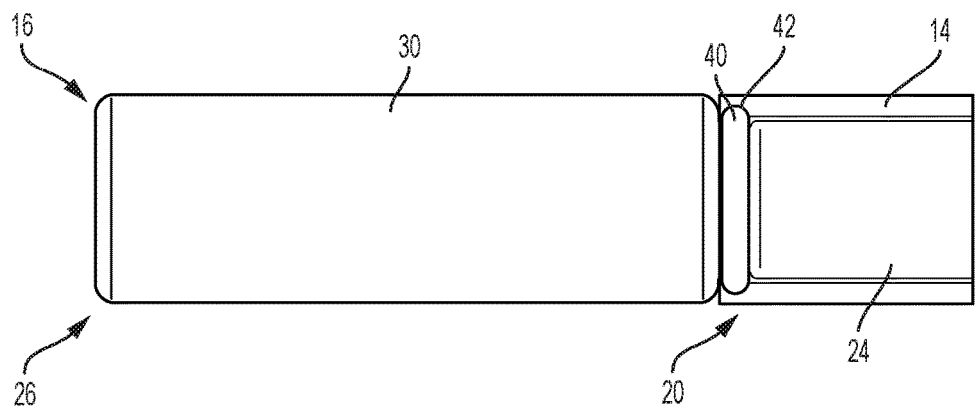
FIG. 5 is a detail side view of the proximal ends of the sample brush and the sleeve shown in FIG. 1, illustrating mechanical connection between the brush and the sleeve.

With reference next to FIG. 4, which shows the proximal end 26 of the sample brush shaft 24 in detail view, the shaft can comprise a detent 40 that serves to hold the longitudinal position of the sample brush 12 relative to the outer sleeve 14 illustrated in FIGS. 1 and 2. More particularly, the detent 40 is sized and configured to be received by a recess 42, shown in FIG. 5, which is formed inside the outer sleeve 14 at its proximal end 20. In such cases, the sample brush 12 will not linearly translate relative to the outer sleeve 14 unless the user overcomes the force that holds the detent 40 within the recess 42.

FIGS. 1 and 2 show the cell collection device 10 in its initial position (a first orientation of the device) prior to use. In this orientation, the sleeve 14 is positioned proximally so that the proximal end 20 of the sleeve contacts or nearly contacts the grip element 30 of the brush 12. In that position, the tip 36 and bristles 34 of the brush 12 extend beyond the distal end 22 of the sleeve 14 and are prepared for insertion into the patient. To collect cells from the patient, the distal end of the device 10 is inserted into the patient's anus to the point at which the bristles 34 of the sample brush 12 are no longer visible. If insertion of the brush 12 is halted at that point, the bristles 34 will be positioned at the anorectal transformation zone at which cell collection is desired. At that point, the brush 12 can be rotated about its longitudinal axis while the sleeve 14 is held stationary. Such relative rotation can be achieved by gripping the stick grip element 30 with one hand and gripping the sleeve 14 with the other hand. Once the brush 12 has passed through one or more revolutions, the sample brush 10 can be withdrawn from the patient.

Figure 6:
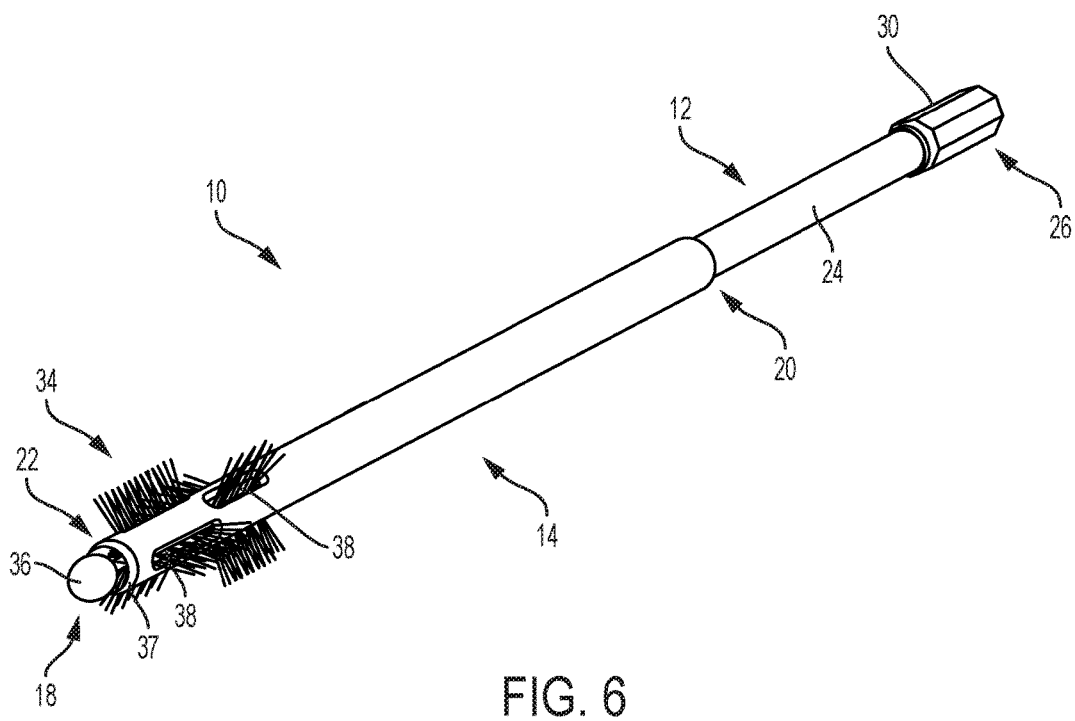
FIG. 6 is a further perspective view of the device of FIG. 1, showing the distal end of the sample brush withdrawn within the sleeve to facilitate cell transfer.

Once the cell collection device 10 has been removed from the patient, the sleeve 14 can be pushed distally along the length of the brush 12 (overcoming the connection provided by the detent 40) so that the sleeve will encapsulate the bristles 34 of the brush, as shown in FIG. 6. As the brush 12 is retracted into the sleeve 14, the beveled edge 37 of the sleeve 14 scrapes the bristles 34 as they collapse into the sleeve to remove collected cells from them. Once the bristles 34 are sheathed within the sleeve 14 (a second orientation of the device 10), some bristles will extend through the bristle windows 38. Notably, the tapered portion 32 of the stick shaft 24 provides room for the bristles within the sleeve 14 and prevents binding between the brush 12 and the sleeve 14.

After the bristles 34 have been pulled into the sleeve 14, the distal ends of the sample brush 12 and the sleeve can be immersed in a cell collection medium, such as a suitable liquid. The brush 12 can then be rotated relative to the sleeve 14 or vice versa to transfer the collected cells from the bristles 34 to the collection medium. During this rotation, some bristles 34 will extend through the windows 38 while others that were extending through the windows will be retracted back into the sleeve 14. This alternate extension and retraction, and the beveled edges 39 of the windows 38, facilitates transfer of the collected cells to the collection medium. After several rotations, for example, back-and-forth rotations, have been performed, the cell collection device 10 can be removed from the collection medium and discarded.

The cell collection device 10 described above provides several advantages over the swabs that are currently used for anal cancer screening. First, the collection process is greatly simplified. Because of the optimized length and diameter of the insertion section of the sample brush 12, cells can be collected from the desired region (e.g., the anorectal transformation zone) without guesswork. Because of the length and distribution of the bristles 34, cells can be collected with as little as a single rotation of the brush 12 and without lateral pressure or repeated passes. As a result, the sample process can be standardized and variability in the results from physician to physician can be minimized. Furthermore, the sleeve 14 provides for encapsulation of the bristles after insertion and the relative rotation of the sleeve and the brush 12 enables easy and safe transfer of the collected cells from the bristles 34 to the collection medium. Moreover, the shape of the brush tip 36, the nature of the bristles 34, and the manner in which the brush 10 is manipulated to collect cells translates into improved patient comfort during the cell collection procedure.

The invention claimed is:

1. A method for collecting cells from an anus of a patient, the method comprising:
   obtaining a cell collection device comprising a sample brush including an elongated shaft having a distal end and radially extending bristles provided at the distal end and a tubular outer sleeve through which the elongated shaft extends, the outer sleeve including a distal end including a distal tip having a distal opening from which the distal end of the elongated shaft and its bristles extend;
   inserting the distal end of a sample brush extending from the distal tip of the outer sheath into the anus;
   rotating the sample brush while the distal end of the brush is within the anus to collect cells with bristles provided at the distal end of the brush;
   withdrawing the sample brush from the anus;
   linearly moving the outer sleeve relative to the sample brush or vice versa such that the bristles of the brush extending from the distal opening of the outer sleeve are retracted into the outer sleeve;
   inserting the distal end of the outer sleeve along with the bristles into a cell collection liquid; and
   rotating the sample brush relative to the outer sleeve or vice versa to enable the bristles of the brush to alternately extend from bristle windows positioned at the distal end of the outer sleeve and retract into the outer sleeve, wherein the extension and retraction of the bristles causes cells collected by the bristles to transfer to the cell collection liquid.

2. The method of claim 1, wherein the distal tip of the outer sleeve has a beveled edge that facilitates removal of cells from the bristles.

3. The method of claim 1, wherein the bristle windows have beveled edges that facilitate removal of cells from the bristles.

* * * * *